United States Patent [19]

Wiedemann et al.

[11] Patent Number: 4,666,812
[45] Date of Patent: May 19, 1987

[54] ELECTROPHOTOGRAPHIC MATERIAL WITH PYRIMIDO-PYRIDOBENZIMIDAZOLE COMPOUND

[75] Inventors: Wolfgang Wiedemann, Geisenheim-Johannisberg; Dieter Guenther, Kelkheim, both of Fed. Rep. of Germany

[73] Assignee: Hoechst Aktiengesellschaft, Frankfurt am Main, Fed. Rep. of Germany

[21] Appl. No.: 822,153

[22] Filed: Jan. 24, 1986

[30] Foreign Application Priority Data

Jan. 26, 1985 [DE] Fed. Rep. of Germany ....... 3502681

[51] Int. Cl.$^4$ .......................... G03G 5/06; G03G 5/09
[52] U.S. Cl. ........................................ 430/78; 430/76; 430/77; 430/83
[58] Field of Search ...................... 430/58, 59, 76, 77, 430/78, 83

[56] References Cited

U.S. PATENT DOCUMENTS

| | | | |
|---|---|---|---|
| 3,870,516 | 3/1975 | Smith et al. | 430/58 X |
| 3,973,959 | 8/1976 | Rochlitz et al. | 430/58 |
| 3,992,205 | 11/1976 | Wiedemann | 430/77 X |
| 4,153,461 | 5/1979 | Berghaeuser et al. | |

FOREIGN PATENT DOCUMENTS

| | | | |
|---|---|---|---|
| 25891 | 8/1972 | Australia | 430/83 |
| 2929414 | 2/1981 | Fed. Rep. of Germany | |
| 58-156940 | 9/1983 | Japan | 430/78 |
| 59-26738 | 2/1984 | Japan | 430/78 |

*Primary Examiner*—Roland E. Martin
*Attorney, Agent, or Firm*—Schwartz, Jeffery, Schwaab, Mack, Blumenthal & Evans

[57] ABSTRACT

The photoconductor of an electrophotographic recording material comprising an electrically conductive support, an optional insulating interlayer, and a photoconductive single layer containing a binder, a dye or pigment sensitizer and a pyrimido[5′,4′:5,6]pyrido[1,2-a]benzimidazole charge transporting compound represented by the formula

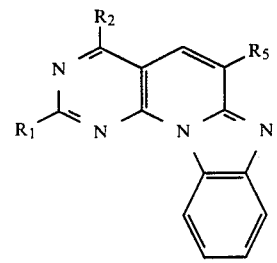

wherein $R_1$ and $R_2$ are identical or different and are hydrogen or an $R_3,R_4N$ group; $R_3$ and $R_4$ are identical or different and are ($C_1$ to $C_4$)-alkyl, hydroxy-($C_1$ to $C_4$)-alkyl, phenyl or benzyl which are unsubstituted or ($C_1$ to $C_4$)-alkyl-substituted, or, together with the N atom to which they are bonded, are an imidazolyl or triazolyl group; and $R_5$ is a benzothiazole, a benzoxazole or a benzimidazole group, is photosensitive in the visible range around 430 to 500 nm and can be sensitized for the longer-wavelength region with dyes.

8 Claims, 7 Drawing Figures

ELECTROPHOTOGRAPHIC MATERIAL WITH PYRIMIDO-PYRIDOBENZIMIDAZOLE COMPOUND

BACKGROUND OF THE INVENTION

The present invention relates to an electrophotographic recording material comprised of an electrically conductive support, an optional insulating interlayer, and a photoconductive single layer containing a pyrimido[5',4':5,6]pyrido-[1,2a]benzimidazole derivative as the photoconductor, a binder, and a dye or pigment in homogeneous solution or disperse distribution as a sensitizer. The present invention relates in particular to an electrophotographic recording material for a lithographic printing form or a printed circuit, that can be prepared by an electrophotographic method when binders which can be stripped under alkaline conditions are present in the photoconductive layer.

Certain pyrimido[5',4':5,6]pyrido-[1,2a]benzimidazole compounds are known. These have been generally described in German Offenlegungsschrift No. 2,929,414 as fluorescent brighteners, as fluorescence dyes, and even as photoconductors. Their unusually good photoconductive properties in binders which can be stripped, especially under alkaline conditions, were neither described nor suggested, however. Instead, the range of application of the compounds was very restricted, due to their low solubility properties and poor film-forming properties.

The maximum absorption of most of the compounds known as organic photoconductors, such as oxazole, oxadiazole, pyrazoline and phenylhydrazone derivatives and also polyvinylcarbazole, is below the 400 nm wavelength. In the presence of binders, the photoconductive layers are in most cases transparent to light in the spectral region above 430 nm, so that, without sensitization, they are photosensitive only in the near-ultraviolet region.

SUMMARY OF THE INVENTION

It is therefore an object of the present invention to provide organic photoconductive compounds that, in combination with suitable binders, particularly binders that can be stripped under alkaline conditions, ensure homogeneous film formation and good photosensitivity, especially in the region of the visible spectrum from about 430 to 500 nm.

It is also an object of the present invention to provide photoconductive layers comprised of the aforesaid organic compounds, which layers possess a photosensitivity that can be spectrally expanded by means of sensitizers and/or pigments.

It is yet another object of the present invention to provide an electrophotographic recording material comprising a photoconductor that is photosensitive in the spectral range around 430 to 500 nm and that can be sensitized, with dyes or pigments, to longer-wavelength irradiation.

In accomplishing the foregoing objects, there has been provided, in accordance with one aspect of the present invention, an electrophotographic recording material comprising an electrically conductive support and a photoconductive layer provided on said support, said photoconductive layer containing (i) a pyrimido[5',4':5,6]pyrido[1,2-a]benzimidazole charge transporting compound (ii) a binder and (iii) a dye or pigment sensitizer, wherein said charge transporting compound is represented by the formula wherein
- $R_1$ and $R_2$ are identical or different and are each hydrogen or an $R_3R_4N$ group;
- $R_3$ and $R_4$ are identical or different and (i) are each (a) alkyl having 1 to 4 carbon atoms, (b) hydroxyalkyl having 1 to 4 carbon atoms, or (c) phenyl or benzyl which is unsubstituted or substituted by an alkyl group having 1 to 4 carbon atoms, or (ii) together with the N atom to which they are bonded, are an imidazolyl or a triazolyl group; and
- $R_5$ is a benzothiazole, a benzoxazole or a benzimidazole group.

In a preferred embodiment, the charge transporting compound used in the photoconductive layer is represented by the formula Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

In contrast to the benzimidazole compounds disclosed by German Offenlegungsschrift No. 2,929,414, which are substituted by halogen or ether groups, the compounds according to the present invention can very readily be dissolved and processed into films.

Together with film formers, they have, with positive electrostatic charging, an unusual and surprisingly high characteristic photosensitivity, which makes them particularly suitable for certain laser light sources, such as He/Cd and Ar lasers, that emit in the spectral region up to 500 nm. The photoconductive compounds of the present invention can be used with film formers, such as polyvinyl acetals, polyester resins and vinyl chloride/vinyl acetate copolymers, for electrophotographic microfilm recording materials. Together with binders that can be stripped under alkaline conditions, such as copolymers of styrene and maleic anhydride or vinyl acetate, (meth)acrylates and crotonic acid, and phenolic resins, singly or as a mixture, these photoconductive compounds can be processed to give positively chargeable, photosensitive layers for printing forms or printed circuits.

The spectral sensitivity range of the electrophotographic recording materials according to the present invention can be further influenced, depending on the application, by sensitizers or by photoactive pigments which are homogeneously dissolved or dispersed, respectively, in the photoconductive layer.

The preparation and characterization of the photoconductive compounds according to the present invention is disclosed in German Offenlegungsschrift No. 2,929,414. The compound represented by formula I above can also be reacted by condensation with formaldehyde to give a polycondensate which, in addition to good film-forming properties, also has a high photosensitivity.

The photoconductive compounds of the present invention can be dissolved together with a number of binders and processed to give homogeneous films. The charge transporting compound-to-binder mixing ratio is preferably 1:1. This ratio is limited by the crystallization of the charge transporting compound, in the case of an excessively high concentration of photoconductor (greater than 50% by weight), and by a lower photosensitivity, in the case of too low a content (less than 25% by weight) in the particular binder.

Figure 1:
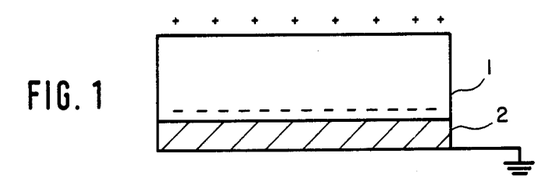
FIGS. 1, 2 and 3 are schematic drawings that provide, respectively, cross-sectional views of three photoconductor layers within the present invention.
Figure 2:
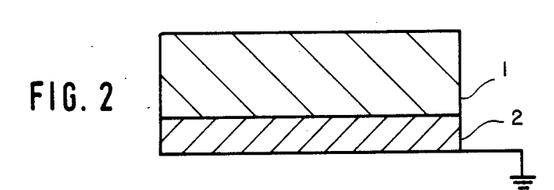
Figure 3:
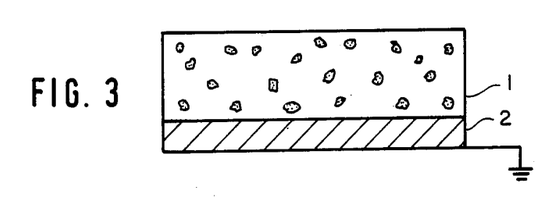

With reference to FIGS. 1 through 3, a photoconductive layer 1 provided on an electrically conductive support 2, in accordance with the present invention, can be present in the unsensitized state (FIG. 1); in the homogeneously sensitized state, preferably with homogeneously dissolved sensitizers or acceptor additives, e.g., as shown in FIG. 2; or with pigment additives dispersed through the layer as charge carrier-generating centers (FIG. 3).

Figure 4:
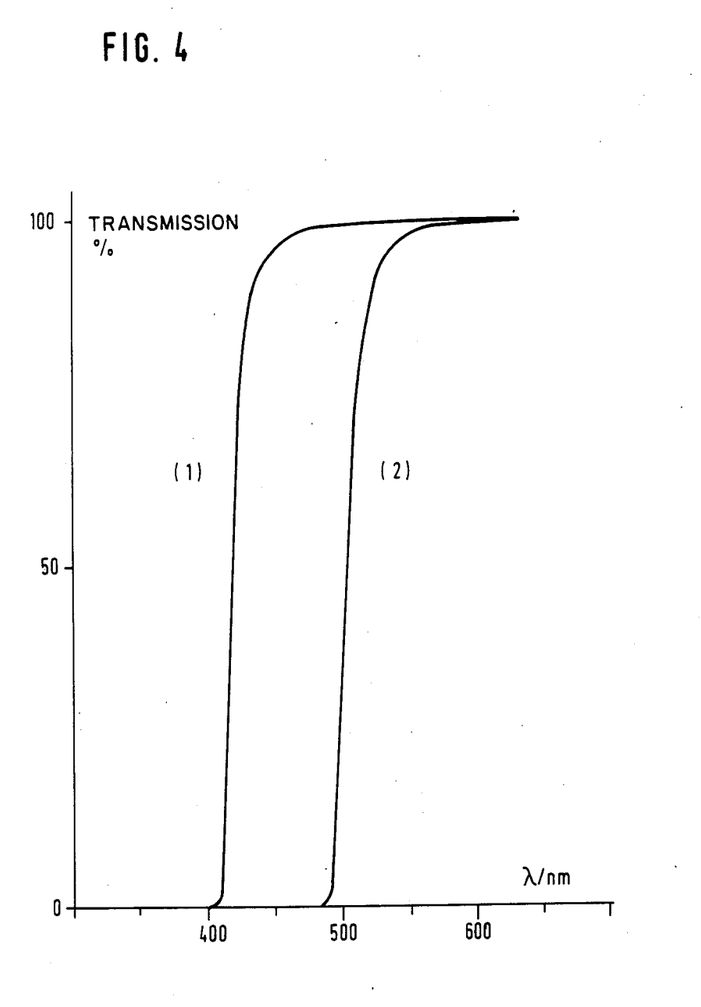
FIG. 4 is a graph showing the relationship between absorptivity (percent transparency) and the wavelength of radiation to which a photoconductive layer according to the present invention and a prior-art photoconductive layer are exposed, respectively.

The high absorptivity of the photoconductive layers according to the present invention in the visible wavelength region up to about 500 nm is illustrated in FIG. 4 (curve 2).

The absorption maximum of the compound of formula II is shown to be 431 nm, with a secondary maximum at 455 nm. For comparison, a film was also prepared from the same binder and 2,5-bis-(4-diethylaminophenyl)-1,3,4-oxadiazole, the transmission of which rises steeply from about 425 nm (curve 1).

The high photosensitivity under positive charging of a photoconductive layer according to the present invention can be explained by absorption, excitation and charge generation, under the action of the electric field, involving photoconductor molecules in an upper "excitation" zone of the layer. The extent of the excitation zone depends on the depth of penetration of the light into the photoconductive layer (see FIG. 7).

Figure 7:
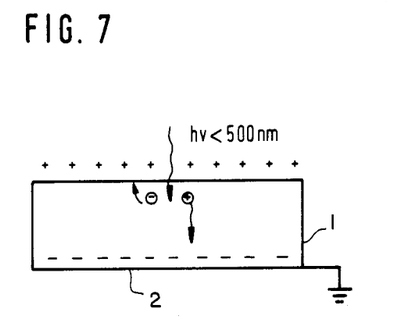
FIG. 7 is a schematic drawing illustrating a proposed mechanism for photosensitivity under positive charging of a photoconductive layer according to the present invention.

Because of the p-conductive character (i.e., conduction by formation and transport of free-radical cations) of these photoconductive compounds, the defect electrons which are generated are more readily transported over a wider range of thicknesses, according to the scheme:

| $h\nu < 500$ nm | |
|---|---|
| $PC \rightarrow PC^*$ | excitation |
| $PC^* \rightarrow \cdot PC^{\oplus} + \ominus$ | (charge carrier generation) |
| $\cdot PC^{\oplus} + PC \rightarrow PC + \cdot PC^{\oplus}$ | (charge transport) |

All the materials conventionally used for supports, in particular for the preparation of printing forms by electrophotographic means, can likewise be used for this purpose in the present invention. For example, aluminum, zinc, magnesium and copper foils or plates, or multi-metal plates, can be used as supports. Plastics, such as polyamides in film form or films with vapor-deposited metal, can also be employed for supports. Surface-treated aluminum foils have proved particularly suitable. The surface treatment comprises mechanical or electrochemical roughening and, if appropriate, subsequent anodizing and treatment with silicate or with polyvinyl-phosphonic acid in accordance with German Offenlegungsschrift No. 1,621,478 (corresponding to U.S. Pat. No. 4,153,461).

In addition, aluminum-laminated metal foils or polyester films with vapor-deposited aluminum can be used for copying materials. Transparent films rendered conductive with, for example, palladium- or indium-tin oxide, and special papers can also be used for electrophotographic microfilm recording materials.

The insulating intermediate layer which is optionally present in conventional electrophotographic recording materials can also be provided between a support and a photoconductive layer of the present invention. Such an intermediate layer can be formed from organic synthetic resins, such as polyurethanes, in thin-layer thickness.

Suitable binders preferred by virtue of their film properties and adhesive strength include natural or synthetic resins, in particular polyester resins, polycarbonates, polyurethanes, vinyl chloride/vinyl acetate copolymers, polyvinyl acetals, polyvinyl acetates, cellulose acetobutyrates, silicone resins, poly(meth)acrylates, cellulose nitrates, rubber and rubber derivatives such as chlorinated rubber and cyclized rubber, and the like. In addition to the film-forming and electrical properties and those properties relating to strength of adhesion to the support, solubility properties play an important role in the selection of binders for use in printing forms and printed circuits. For practical purposes, those binders which are soluble in aqueous or alcoholic solvent systems, with or without addition of acid or alkali, are particularly suitable. Accordingly, suitable binders are high-molecular substances that carry groups conferring alkali solubility. Examples of such groups are acid anhydride, carboxyl, phenol, sulfo, sulfonamide and sulfonimide.

Copolymers with anhydride groups can be used particularly successively since, coupled with good alkali solubility, the conductivity of the photoconductive layer in the dark is low due to the absence of free acid groups. Copolymers of styrene and maleic anhydride, as well as phenolic resins, are very particularly suitable.

Copolymers of styrene, methacrylic acid and methacrylate, having a composition of 1 to 35% of styrene, 10 to 40% of methacrylic acid and 35 to 83% of n-hexyl methacrylate, can also be used as alkali-soluble binders. A terpolymer of 10% of styrene, 30% of methacrylic acid and 60% of n-hexyl methacrylate is outstandingly suitable. Moreover, polyvinyl acetates, in particular copolymers of vinyl acetate and crotonic acid, can be employed.

The photoconductive layer of the present invention essentially contains the above-described organic photoconductive compounds; binders, which can be used singly or in combination; sensitizers and, as the application requires, further conventional additives, such as activators, plasticizers, leveling agents and the like.

To achieve homogeneous sensitization, the organic dyes listed in the Farbstofftabellen [Dye Tables] by Schultz (7th edition, volume 1, 1931) can be used for example. The dyes include triarylmethane dyes such as brilliant green (No. 760, page 314), Victoria blue B (No. 822, page 347), methyl violet (No. 783, page 327), crystal violet (No. 785, page 329) and acid violet 6B (No. 381, page 351); xanthene dyes, namely rhodamines, such as rhodamine B (No. 864, page 365), rhodamine 6G (No. 866, page 366), rhodamine G extra (No. 865, page 366), sulforhodamine B (No. 863, page 364) and Echtsaeureeosin [acid-fast eosin] G (No. 870, page 368); phthaleins such as eosin S (No. 883, page 375), eosin A (No. 881, page 374), erythrosin (No. 866, page 376), phloxin (No. 890, page 378), Rose Bengale (No. 889, page 378) and fluorescein (No. 880, page 373); thiazine dyes such as methylene blue (No. 1038, page 449), acridine dyes such as acridine yellow (No. 901, page 383), acridine orange (No. 908, page 387) and trypaflavin (No. 906, page 386); quinoline dyes such as pinacyanol (No. 924, page 396) and cryptocyanine (No. 927, page 397); quinone dyes and ketone dyes such as alizarin (No. 1141, page 449), alizarin red S (No. 1145, page 502) and quinizarin (No. 1148, page 504); and cyanine dyes (polymethine dyes) such as Astrazon yellow 3G (Color Index No. (C.I.) 48,055) and 5G (C.I. 48,065), basic yellow 52115 (C.I. 48,060), Astrazon yellow GRL, Astrazon orange G (C.I. 48,040) and R (C.I. 48,035) and Astrazon orange 3R (not yet classified).

Pyrylium salts, thiapyrylium salts and benzopyrylium salts can also be used.

The preferred dyes used in a photoconductive layer of the present invention are those that absorb in the region from 500 to 750 nm, but dyes with an absorptive region from about 400 to 500 nm can also have a sensitivity-enhancing effect. Mixtures of sensitizing dyes can also be present.

Metal-containing or metal-free phthalocyanine pigments, for example, copper phthalocyanine, perinone, thioindigo, polycyclic quinone, quinacridone, perylene, anthraquinone, dioxazine, azo, bisazo, trisazo and cyanine pigments, or benzo(thio)-xanthene derivatives and their mixtures can also be used as dyes or pigments in disperse distribution. Particularly preferred amongst these are phthalocyanine pigments, such as the various Cu phthalocyanine modifications ($\alpha$, $\psi$ and $\epsilon$), bis- and tris-azo pigments, perylimide pigments and condensation products of perylene-3,4,9,10-tetracarboxylic acid anhydride and aromatic diamines, such as o-phenylenediamine, for example perylene-3,4,9,10-tetracarboxylic acid diimide-bisbenzimidazoles, or (iso)violanthrones. They can be present in the amounts of up to 30%, relative to the total mass of the photoconductive layer, and preferably quantities in the range from 0.1 to 10% pigment are used.

The layer thickness of the photoconductor layer is not critical, and is generally in the range from 2 to 20 $\mu$m. But depending on the application, these limits can be adjusted upward or downward.

The examples that follow are intended to illustrate, without restricting, the invention in more detail.

EXAMPLE 1

A 10% solution comprising 50 parts by weight of the compound represented by formula II and 50 parts by weight of polyvinyl butyral (Mowital B30H) in tetrahydrofuran (THF) was whirler-coated to different layer thicknesses onto a polyester film carrying vapor-deposited aluminum. The coating was then dried for 5 minutes at 90° to 100° C.

The photosensitivity of these homogeneous photoconductive layers was measured as follows:

To determine the characteristic photodischarge curve of a photoconductive layer thus prepared, a given test sample was moved on a rotating dish through a charging device to the exposure station, where it was continuously exposed with an XBO 150 xenon lamp. A heat-absorbing glass and a neutral filter was placed in front of the lamp. The light intensity in the measurement plane was about 25 $\mu$W/cm$^2$. The charge level and the photoinduced decay curve were recorded oscillographically, using an electrometer, by means of a transparent probe. The photoconductor layer was characterized by the charge level ($U_o$) and the time ($T_{\frac{1}{2}}$) after which half the charge ($U_o/2$) had been reached. The product of $T_{\frac{1}{2}}$ and the measured light intensity I ($\mu$W/cm$^2$) is the half-value energy $E_{\frac{1}{2}}$ ($\mu$J/cm$^2$).

The following results were obtained from photosensitivity measurements conducted as described above:

| Layer weight (g/m$^2$) | $U_o$(V) | $E_{\frac{1}{2}}$ |
|---|---|---|
| 4.7 | (−) 580 | 49 |
| (about 4 $\mu$m) | (+) 730 | 8.0 |
| 8.0 | (−) 780 | 65 |
| (about 7 $\mu$m) | (+) 710 | 11.5 |

EXAMPLE 2

For about 5 hours in a ball mill 5 parts of N,N'-dimethylperylimide (C.I. pigment red 179) were very finely ground in a solution comprised of 47.5 parts of the compound of formula II and 47.5 parts of a copolymer of styrene and maleic anhydride (Scripset 540). The pigment dispersion was then coated to 4 to 5-$\mu$m thickness onto wire-brushed aluminum foil (100 $\mu$m) (layer No. 1). In the same way, a finely dispersed solution comprising equal parts of the aforesaid compound, the copolymer (Scripset 540) and 2.5 parts of metal-free phthalocyanine (C.I. 74,100, Monolite fast blue GS) was prepared. The resulting dye dispersion was whirler-coated, to a thickness of about 5 μm after drying, onto both wire-brushed (No. 2) and anodized aluminum foil (layer No. 2).

The photosensitivity of the prepared layers, measured as in Example I, is shown in the following table:

| Layer No. | (+) U$_o$/V | E$_\frac{1}{2}$ | (−) U$_o$(V) | E$_\frac{1}{2}$ |
|---|---|---|---|---|
| 1 | 310 | 6.8 | 420 | 9.6 |
| 2 | 340 | 10.9 | — | |
| 3 | 530 | 12.1 | — | — |

EXAMPLE 3

Soluble sensitizing dyes, such as rhodamine B and crystal violet, were added in a weight ratio (relative to the photoconductive compound) of 1:500 to a solution comprising equal parts by weight of the compound of formula II and polyvinyl butyral (Mowital B30H) in THF. The resulting homogeneous dye solutions were whirler-coated in 7- to 8-μm thicknesses onto aluminum foil.

The measurements of the photosensitivity of these sensitized layers gave the following values:

| Layer (sensitizer) | (+) U$_o$(V) | E$_\frac{1}{2}$ | (−) U$_o$/V | E$_\frac{1}{2}$ |
|---|---|---|---|---|
| 1 — | 780 | 11.0 | | |
| 2 Rhodamine B | 820 | 9.2 | | |
| 3 Crystal violet | 820 | 7.3 | 710 | 19.1 |

The spectral photosensitivity of Layers 1 and 3, respectively, was determined as in Example 1, with interference filters placed in front of the exposure lamp.

With a positive charge (800 to 850 V), the half-life (T$_\frac{1}{2}$ in msec) for the particular wavelength range is determined by exposure. Plotting of the reciprocal half-value energy (1/E$_\frac{1}{2}$) over the wavelength λ in nm gives the spectral photosensitivity curve. The half-value energy (E$_\frac{1}{2}$) denotes the light energy that must be radiated to discharge the irradiated layer to half the initial voltage (U$_o$).

Figure 5:
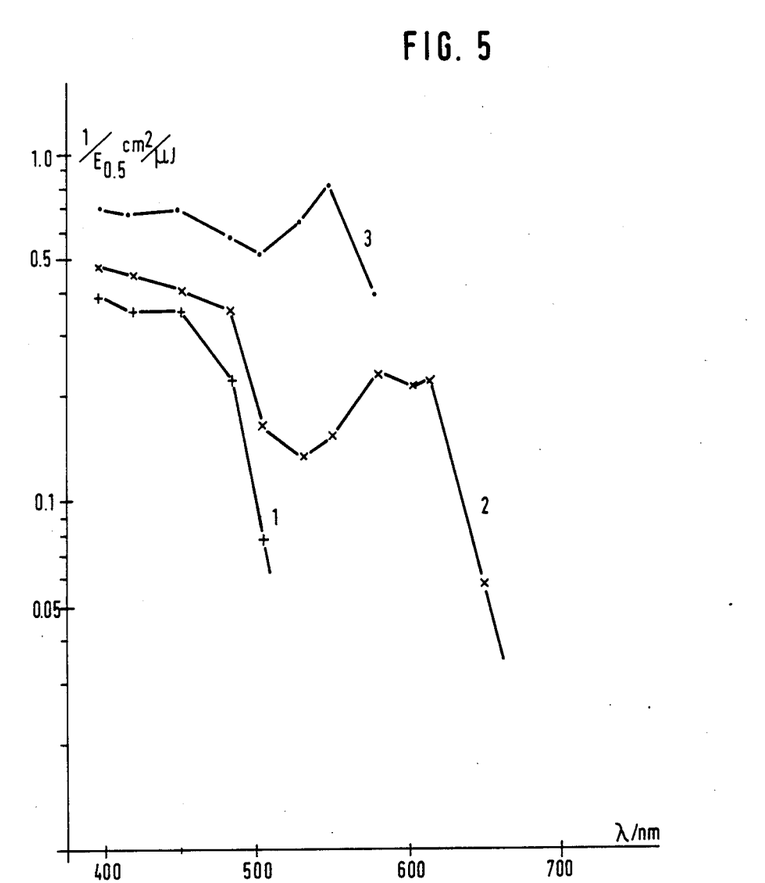
FIGS. 5 and 6 are each graphs that depict the spectral photosensitivity of various photoconductive layers, with and without a sensitizer, prepared in accordance with the present invention.

FIG. 5 shows the spectral photosensitivities, in the case of a positive charge, of photoconductive layers without (curve 1) and with (curve 2) the sensitizer a crystal violet.

EXAMPLE 4

Various sensitizers, such as crystal violet, astrazon orange R or brilliant green, were added to a solution containing 65 parts of the compound of formula II and 35 parts of cellulose nitrate H4 in THF, in the ratio of 1:50 relative to the photoconductive compound. The solution thus prepared was whirler-coated to a thickness of 6 to 7 μm (dry) onto wire-brushed aluminum foil.

After drying of the layers, the following photosensitivities, determined as in Example 1, were measured:

| Layer with sensitizer | (+) U$_o$(V) | E$_\frac{1}{2}$ |
|---|---|---|
| — | 670 | 12.9 |
| Crystal violet | 690 | 2.5 |
| Astrazon orange R | 710 | 3.3 |

| Layer with sensitizer | (+) U$_o$(V) | E$_\frac{1}{2}$ |
|---|---|---|
| Brilliant green | 650 | 6.2 |

EXAMPLE 5

Different quantities of rhodamine B sensitizer (relative to the compound of formula II) were added to a coating solution as described in Example 4, and homogeneous photoconductor layers of a thickness between about 6 and 7 μm were prepared from this solution.

The photosensitivity was measured using the method of Example 1:

| Layer with rhodamine B ratio | (+) U$_o$(V) | E$_\frac{1}{2}$ | (−) U$_o$/V | E$_\frac{1}{2}$ |
|---|---|---|---|---|
| — | 630 | 11.8 | 650 | 30 |
| 1:1000 | 610 | 5.4 | 500 | 18.9 |
| 1:500 | 680 | 3.8 | 710 | 11.2 |
| 1:100 | 670 | 2.4 | 640 | 7.1 |
| 1:50+ | 640 | 2.1 | 680 | 7.2 |
| 1:10 | 660 | 2.6 | 630 | 25.0 |

+ The spectral photosensitivity, with a positive charge (600 V), of the photoconductor layer with the 1:50 sensitizing ratio was determined as in Example 3 (FIG. 5, curve 3).

EXAMPLE 6

Different quantities of rhodamine B sensitizer were added to a solution comprising equal parts by weight of the compound of formula II and a styrene/maleic anhydride copolymer (Scripset 540) in THF. The homogeneous solution was then whirler-coated to a thickness of about 5 μm onto wire-brushed aluminum foil. The photosensitivity of the layers was determined according to Example 1:

| Layer with rhodamine B ratio | (+) U$_o$(V) | E$_\frac{1}{2}$ |
|---|---|---|
| —+ | 710 | 7.3 |
| 1:500 | 710 | 6.6 |
| 1:100 | 680 | 5.1 |
| 1:50+ | 770 | 4.5 |

Figure 6:
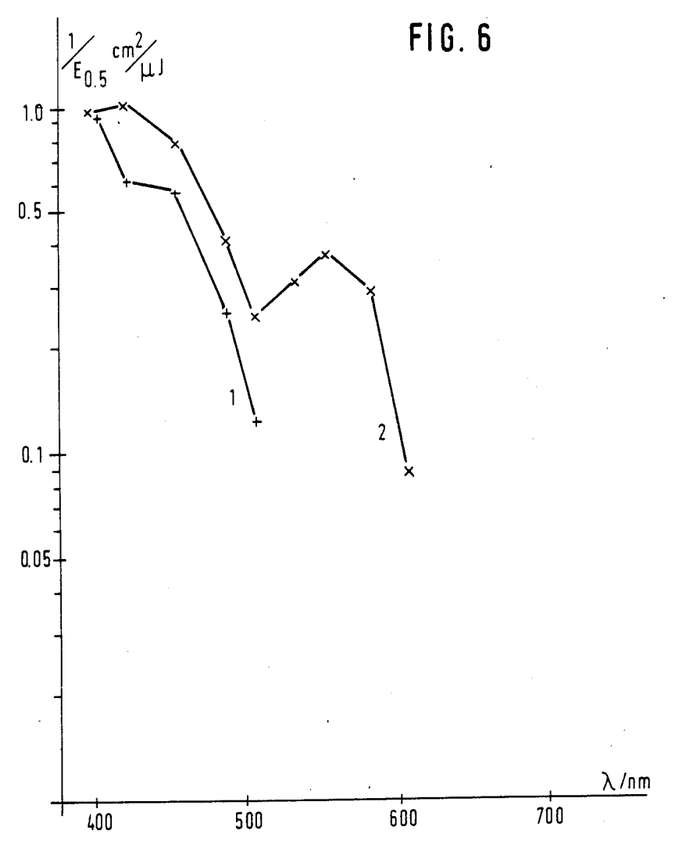

⊕The respective spectral photosensitivity curves of the unsensitized and the 1:50-sensitized photoconductor layers were determined at a positive charge of about 500 V (see FIG. 6, curves 1 and 2, respectively).

COMPARISON EXAMPLE

The known photoconductive compounds 2,5-bis-(4'-diethylaminophenyl)-1,3,4-oxadiazole (A), 2-phenyl-4-(2-chlorophenyl)-5-(4'-diethylaminophenyl)-oxazole (B) and 2-vinyl-4-(2'-chlorophenyl)-5-(4'-diethylaminophenyl)-oxazole (C) were whirler-coated in the same composition as described in Example 6, and under sensitization conditions (1:500), to a thickness of about 5 μm onto the same support material. Measurement of the photosensitivity of the resulting layers gave the following values:

| Photoconductor layer (Rhodamine B) | (+) U$_o$(V) | E$_\frac{1}{2}$ |
|---|---|---|
| A | 650 | 25.9 |
| + (1:500) | 700 | 12.7 |
| B | 590 | 17.9 |
| + (1:500) | 670 | 9.0 |

-continued

| Photoconductor layer (Rhodamine B) | (+) $U_o(V)$ | $E_½$ |
|---|---|---|
| C | 640 | 35.6 |
| + (1:500) | 830 | 12.5 |

EXAMPLE 7

The compound of formula II (0.01 mol) was reacted for about 2 hours under mild conditions (below 40° C.) with paraformaldehyde (0.01 mol) in glacial acetic acid, with the addition of 0.5 g of anhydrous $ZnCl_2$. After the inorganic constituents and the insoluble and monomeric organic fractions had been separated off, the soluble fraction (less than 20%) was used for casting a homogeneous film of about 2 μm in thickness onto wire-brushed aluminum foil.

Measurement of the photosensitivity with a positive charge of 190 V gave an $E_½$ value of 4.65 μJ/cm².

What is claimed is:

1. An electrophotographic recording material comprising an electrically conductive support and a photoconductive layer provided on said support, said photoconductive layer containing (i) a pyrimido[5',4':5,6-]pyrido[1,2-a]benzimidazole charge transporting compound, (ii) a binder and (iii) a dye or pigment sensitizer, wherein said charge transporting compound (A) is represented by the formula

I wherein
$R_1$ and $R_2$ are identical or different and are each hydrogen or an $R_3R_4N$ group;
$R_3$ and $R_4$ are identical or different and (1) are each
(a) alkyl having 1 to 4 carbon atoms, (b) hydroxyalkyl having 1 to 4 carbon atoms, or (c) phenyl or benzyl which is unsubstituted substituted by an alkyl group having 1 to 4 carbon atoms, or (2), together with the N atom to which they are bonded, are an imidazolyl or a triazolyl group; and
$R_5$ is a benzothiazole, a benzoxazole or a benzimidazole group,
and (B) is present in said photoconductive layer in an amount ranging between about 25% and 65% by weight, relative to said binder.

2. A recording material as claimed in claim 1, wherein said charge transporting compound is represented by the formula

II

3. The recording material as claimed in claim 1, wherein said binder is soluble under alkaline conditions.

4. A recording material as claimed in claim 3, wherein said binder comprises at least one selected from the group consisting of a copolymer of styrene and maleic anhydride, a copolymer of vinyl acetate and crotonic acid, and a phenolic resin.

5. A recording material as claimed in claim 1, wherein said photoconductive layer contains a homogeneously dissolved dye sensitizer.

6. A recording material as claimed in claim 1, wherein said photoconductive layer contains a pigments in disperse distribution.

7. A recording material as claimed in claim 1, further comprising an insulating intermediate layer interposed between said support and said photoconductive layer.

8. A recording material as claimed in claim 1 wherein said amount of said charge transporting compound is between about 25% and 50% by weight.

* * * * *